United States Patent [19]
Tsuboi et al.

[11] Patent Number: 5,952,338
[45] Date of Patent: Sep. 14, 1999

[54] AGENT FOR PROPHYLAXIS AND TREATMENT OF DISTURBANCE OF VISUAL FUNCTION

[75] Inventors: Toshiharu Tsuboi, Settsu; Noriko Watanabe, Suita; Takahiro Ogawa, Nishinomiya; Mitsuyoshi Isaka; Mitsunori Waki, both of Kobe, all of Japan

[73] Assignees: Takeda Chemical Industries, Ltd.; Senju Pharmaceutical Co., Ltd., both of Osaka, Japan

[21] Appl. No.: 08/886,270

[22] Filed: Jul. 1, 1997

[30] Foreign Application Priority Data

| Jul. 5, 1996 | [JP] | Japan | 8-176933 |
| Aug. 13, 1996 | [JP] | Japan | 8-213941 |
| Nov. 25, 1996 | [JP] | Japan | 8-314033 |

[51] Int. Cl.$^6$ .................................................. A61K 31/44
[52] U.S. Cl. ............................................. 514/291; 514/912
[58] Field of Search ..................................... 514/291, 912

[56] References Cited

U.S. PATENT DOCUMENTS

| 4,143,042 | 3/1979 | Nohara et al. | 546/89 |
| 4,255,576 | 3/1981 | Nohara et al. | 546/92 |
| 4,267,332 | 5/1981 | Nohara et al. | 546/89 |
| 4,299,963 | 11/1981 | Nohara et al. | 546/89 |
| 4,728,509 | 3/1988 | Shimizu et al. | 424/81 |
| 5,519,030 | 5/1996 | Shigemitsu et al. | 514/291 |

FOREIGN PATENT DOCUMENTS

| 61010587 | 3/1981 | Japan . |
| 61010588 | 3/1981 | Japan . |
| 1577304 | 10/1980 | United Kingdom . |

OTHER PUBLICATIONS

Ogawa et al., "Effects of Amlexanox on Myopia Induced by Instillation of Carbachol in Monkeys," abstract from *Database Biosis, Biosciences Information Service*, 69$^{th}$ Annual Meeting of the Japanese Pharmacological Soc., Nagasaki, Japan, Mar. 20–23, (1996).

Watanabe et al., "Effects of Amlexanox on Myopic Change Induced by Topical Carbachol in Monkeys," abstract from *Database Biosis, Biosciences Information Service*, 1996 Annual Meeting of the Association for Research in Vision and Opthalmolmology, Fort Lauderdale, Florida, Apr. 21–26 (1996).

Retinal Function in Experimental Myopia; Takashi Fujikado, Tatsuya Omoto; Folia Ophthalmol. Jpn. 42: 1189–1194, 1991 Abstract.

*Primary Examiner*—Zohreh Fay
*Attorney, Agent, or Firm*—Leydig, Voit & Mayer, Ltd

[57] ABSTRACT

An agent for the prophylaxis and treatment of disturbance of visual function, which comprises a compound of the formula [I]

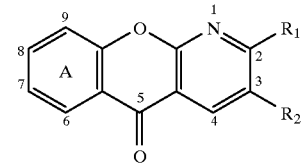

wherein

A ring is optionally substituted;

$R_1$ is a hydrogen or an optionally protected amino; and $R_2$ is a group capable of releasing a proton, or a salt thereof. The agent for the prophylaxis and treatment of disturbance of visual function of the present invention has superior preventive and therapeutic effect on asthenopia, and shows suppression of axial elongation, suppression of degradation of retinal functions and retinal function-recovery action. Hence, the agent can be advantageously used as a clinically applicable agent for the prophylaxis and treatment of disturbance of visual function.

18 Claims, 4 Drawing Sheets

AGENT FOR PROPHYLAXIS AND TREATMENT OF DISTURBANCE OF VISUAL FUNCTION

TECHNICAL FIELD OF THE INVENTION

The present invention relates to an agent for the prophylaxis and treatment of disturbance of visual function. By disturbance of visual function is meant a condition where normal vision cannot be obtained, which condition inclusive of myopia, hypermetropia, strabismus, disorders of retina which is a receptor of light, the condition where normal vision of an object is temporarily prevented by systemic or local fatigue of eyes, and other conditions.

BACKGROUND OF THE INVENTION

Of the disturbances of visual function, myopia and hypermetropia refer to the condition wherein the light that passed through cornea cannot form an image on the retina, and thus cannot grasp the image clearly. Of these, myopia is divided into axial myopia and refractive myopia according to the cause of the condition. The refractive myopia is caused by an increased refraction of cornea and lens, while axial myopia is caused by an elongation of the eyeball in the direction of optic axis, i.e. axial direction. It is nevertheless not easy to simply divide these two. The etiology of myopia has not been fully elucidated and a pharmaceutical agent to completely cure myopia has not been found yet.

In most cases, myopia is treated by a means utilizing correction of optical refraction. Correction of optical refraction by wearing glasses is not an ideal means as far as the quality of life and convenience for studying etc. are concerned. Correction of optical refraction using contact lenses often causes complications, and corneal ulcer may occur, which could possibly lead to the loss of sight in severe cases. In addition, recent application of corneal surgery to cure myopia is sometimes associated with failure to achieve expected levels of refraction, as well as occurrence of pain during operation and postoperative corneal opacity. In view of the fact that the correction of optical refraction and surgical operation such as the above-mentioned cannot be a perfect cure of myopia, treatment of myopia by the use of a drug is desired.

As the pharmaceutical agent to suppress axial elongation, the usefulness of muscarine I receptor antagonist and dopamine receptor agonist has been documented. However, a pharmaceutical agent which can be clinically applied has not been created so far.

Meanwhile, the retina consists of photoreceptor cells, bipolar cells, ganglion cells, horizontal cells, amacrine cells and the like, which transmit optical information to the central nerves. The functions of these cells contribute to the fulfillment of retinal function to organize the received optical information and transmit same to the central nerves.

When the retina is damaged, visual loss, disturbance of light sense and disturbance of visual field are induced, thereby causing central retinal artery and vein occlusions, congenital stationary night blindness, diabetic retinopathy, pigmentary retinal degeneration, retinal detachment, uveitis and the like.

While the therapeutics of retinal diseases and convalescence thereof vary depending on the kind and degree of the diseases, in particular, central retinal artery occlusion, diabetic retinopathy and retinal detachment scarcely allow complete recovery of retinal functions. It may happen that visual acuity does not improve after all and even an operation does not result in full recovery of visual acuity. What is more, no effective cure is currently available for pigmentary retinal degeneration but a symptomatic therapy such as use of sun glasses to avoid direct sun light.

In the internal treatment currently applied to cure retinal diseases, a pharmaceutical agent capable of suppressing degradation of retinal functions and achieving remarkable recovery of retinal function has not been found.

The asthenopia refers to a condition involving a kind of accommodation disorder of ciliary muscle due to systemic or local fatigue of the eye. Fatigue of eyes results in progressively growing distance of near point, which proceeds to the point that the eyes cannot recognize an object temporarily. However, recovery from fatigue can restore the original condition.

The treatment of asthenopia has heretofore included administration of medicaments such as vitamins (e.g., vitamin $B_1$ and vitamin $B_{12}$), ATP and the like, though sufficient therapeutic effects against asthenopia have not been attained.

As mentioned supra, no medicament that purportedly is useful for the prophylaxis and treatment of disturbance of visual function is satisfactory, and the development of an agent for the prophylaxis and treatment of disturbance of visual function has been desired by both doctors and patients.

SUMMARY OF THE INVENTION

According to the present invention, there has now been provided an agent for the prophylaxis and treatment of disturbance of visual function. Thus, the present invention provides:

(1) an agent for the prophylaxis and treatment of disturbance of visual function, which comprises a compound of the formula [I]

wherein
A ring is optionally substituted;
$R_1$ is a hydrogen or an optionally protected amino; and
$R_2$ is a group capable of releasing a proton, or a salt thereof;

(2) the agent for the prophylaxis and treatment of disturbance of visual function according to (1) above, wherein the A ring is optionally substituted by halogen atom, nitro, alkyl, alkoxy or butadienylene (—CH=CH—CH=CH—) which forms a benzene ring with two adjacent carbon atoms at two of the 6, 7, 8 and 9 positions;

(3) the agent for the prophylaxis and treatment of disturbance of visual function according to (1) above, wherein the group capable of releasing a proton is carboxyl or tetrazolyl;

(4) the agent for the prophylaxis and treatment of disturbance of visual function according to (1) above, wherein the compound is represented by the formula [II]

wherein

R is an alkyl;

R₁ is a hydrogen or an optionally protected amino; and

R₂ is a group capable of releasing a proton;

(5) the agent for the prophylaxis and treatment of disturbance of visual function according to (4) above, wherein the alkyl has 1 to 6 carbon atoms;

(6) the agent for the prophylaxis and treatment of disturbance of visual function according to (4) above, wherein the alkyl is isopropyl;

(7) the agent for the prophylaxis and treatment of disturbance of visual function according to (1) or (4) above, wherein $R_1$ is an amino;

(8) the agent for the prophylaxis and treatment of disturbance of visual function according to (1) or (4) above, wherein $R_2$ is a carboxyl;

(9) the agent for the prophylaxis and treatment of disturbance of visual function according to (1) above, wherein the compound is represented by the formula [III]

(10) the agent for the prophylaxis and treatment of disturbance of visual function according to (1) above, which is used for local administration to the eye;

(11) the agent for the prophylaxis and treatment of disturbance of visual function according to (1) above, which is in the form of a liquid preparation;

(12) the agent for the prophylaxis and treatment of disturbance of visual function according to (10) or (11) above, which is in the form of an ophthalmic solution;

(13) the agent for the prophylaxis and treatment of disturbance of visual function according to (12) above, which is in the form of an aqueous ophthalmic solution;

(14) the agent for the prophylaxis and treatment of disturbance of visual function according to (11) above, which is in the form of an injection;

(15) the agent for the prophylaxis and treatment of disturbance of visual function according to (13) or (14) above, which further comprises a solubilizer;

(16) the agent for the prophylaxis and treatment of disturbance of visual function according to (15) above, wherein the solubilizer is polyvinylpyrrolidone;

(17) the agent for the prophylaxis and treatment of disturbance of visual function according to (16) above, wherein the polyvinylpyrrolidone is contained in a concentration of 0.2–20 (W/V) %;

(18) the agent for the prophylaxis and treatment of disturbance of visual function according to any one of (13) to (17) above, which comprises the compound of the formula [I] or a salt thereof in a concentration of 0.01–2.0 (W/V) %;

(19) the agent for the prophylaxis and treatment of disturbance of visual function according to any one of (1) to (18) above, wherein the disturbance of visual function is asthenopia, axial myopia or a retinal disease; and the like.

The compound to be the active ingredient in the present invention is disclosed to have potent antiallergic action and antiinflammatory action in, for example, Japanese Patent Unexamined Publication No. 10587/1986. Japanese Patent Unexamined Publication No. 258083/1995 discloses that the compound to be used in the present invention has prophylactic and therapeutic effects on myopia caused by relaxation of ciliary muscle. It is not until the present invention has been made that the compound to be used in the present invention has been found to have superior prophylactic and therapeutic effects on asthenopia, suppressive action on axial elongation, and therefore, superior prophylactic and therapeutic effects on axial myopia, and suppressive action on degradation of retinal functions and retinal function-recovery action, and therefore, superior prophylactic and therapeutic effects on retinal diseases.

DETAILED DESCRIPTION OF THE INVENTION

In the formula [I], the substituents on the A ring may be, for example, halogen atom, nitro, alkyl, alkoxy, butadienylene (—CH=CH—CH=CH—) which forms a benzene ring with two adjacent carbon atoms at two of the 6, 7, 8 and 9 positions, and the like.

The halogen atom is exemplified by chlorine, bromine, fluorine and the like.

The alkyl is preferably linear or branched alkyl having 1 to 6 carbon atoms. Examples of said alkyl include methyl, ethyl, n-propyl, isopropyl, n-butyl, isobutyl, sec-butyl, tert-butyl, n-pentyl, isopentyl, neopentyl, n-hexyl and the like. More preferred is linear or branched alkyl having 1 to 3 carbon atoms.

The alkoxy preferably has 1 to 4 carbon atoms. Examples of said alkoxy include methoxy, ethoxy, n-propoxy, isopropoxy, n-butoxy, isobutoxy, sec-butoxy, tert-butoxy and the like.

One or more than one, the same or different substituent(s) may be substituted at optional position(s) of the A ring.

In the formulas [I] and [II], the protecting group at $R_1$ of optionally protected amino group is, for example, (1) alkanoyl having 2 to 7 carbon atoms which may have 1 to 3 substituents selected from (a) halogen atom (e.g., chlorine, bromine and fluorine), (b) alkanoyl having 1 to 7 carbon atoms (e.g., formyl, acetyl, propionyl, isopropionyl, n-butyryl, isobutyryl, n-valeryl, isovaleryl, pivaloyl and n-hexanoyl) and (c) nitro, which alkanoyl is exemplified by acetyl, propionyl, isopropionyl, n-butyryl, isobutyryl, n-valeryl, isovaleryl, pivaloyl and n-hexanoyl; (2) arylcarbonyl having 7 to 11 carbon atoms which may have 1 to 3 substituents selected from the above-mentioned (a), (b) and (c), which arylcarbonyl is exemplified by benzoyl, p-toluoyl, 1-naphthoyl and 2-naphthoyl; (3) alkoxycarbonyl having 2 to 7 carbon atoms which may have 1 to 3 substituents selected from the above-mentioned (a), (b) and (c), which alkoxycarbonyl is exemplified by methoxycarbonyl, ethoxycarbonyl, n-propoxycarbonyl, isopropoxycarbonyl and tert-butoxycarbonyl; (4) aryloxycarbonyl having 7 to 11 carbon atoms which may have 1 to 3 substituents selected from the above-mentioned (a), (b) and (c), which aryloxycarbonyl is exemplified by phenoxycarbonyl; (5) aralkylcarbonyl having 8 to 13 carbon atoms which may have 1 to 3 substituents selected from the above-mentioned (a), (b) and (c), which aralkylcarbonyl is exemplified by benzylcarbonyl and phenethylcarbonyl; (6) aralkyloxycarbonyl having 8 to 13 carbon atoms which may have 1 to 3 substituents selected from the above-mentioned (a), (b) and (c), which aralkyloxycarbonyl is exemplified by benzyloxycarbonyl and phenethyloxycarbonyl; (7) phthaloyl optionally having 1 to 3 substituents selected from the above-mentioned (a), (b) and (c), (8) arylsulfonyl having 6 to 10 carbon atoms which may have 1 to 3 substituents selected from the above-mentioned (a), (b) and (c), which arylsulfonyl is exemplified by phenylsulfonyl and tosyl; (9) alkylsulfonyl having 1 to 6 carbon atoms which may have 1 to 3 substituents selected from the above-mentioned (a), (b) and (c), which alkylsulfonyl is exemplified by methylsulfonyl, ethylsulfonyl and n-propylsulfonyl; (10) alkyl having 1 to 6 carbon atoms which may have 1 to 3 substituents selected from the above-mentioned (a), (b) and (c) and amino, which alkyl is exemplified by methyl, ethyl, n-propyl, isopropyl, n-butyl, isobutyl, sec-butyl, tert-butyl, n-pentyl and n-hexyl; (11) aralkyl having 7 to 19 carbon atoms which may have 1 to 3 substituents selected from the above-mentioned (a), (b) and (c), which aralkyl is exemplified by benzyl, phenethyl, benzhydryl and trityl; and the like.

The protecting group at amino includes, for example, alkanoyl having 2 to 7 carbon atoms, arylcarbonyl having 7 to 11 carbon atoms, alkoxycarbonyl having 2 to 7 carbon atoms, aryloxycarbonyl having 7 to 11 carbon atoms, aralkylcarbonyl having 8 to 13 carbon atoms and aralkyloxycarbonyl having 8 to 13 carbon atoms, all of which may have 1 to 3 substituents selected from the above-mentioned (a) halogen atom, (b) alkanoyl having 1 to 7 carbon atoms and (c) nitro.

As $R_1$, preferred is an unsubstituted amino.

In the formulas [I] and [II], the group capable of releasing proton and represented by $R_2$ is exemplified by a group which easily releases $H^+$ and becomes an anion, such as carboxyl, tetrazolyl, trifluoromethanesulfonylamino ($-NHSO_2CF_3$), phosphono and sulfo, which may be any as long as it can release proton under biological or physiological conditions (e.g., reactions in the body such as oxidation, reduction and hydrolysis by biological enzymes) or chemically, or a group capable of converting to such group, and which may be protected by alkyl optionally substituted by a suitable substituent (e.g., alkyl having 1 to 4 carbon atoms such as methyl and n-butyl), optionally substituted acyl (e.g., alkanoyl having 2 to 4 carbon atoms such as acetyl and propionyl which are optionally substituted by halogen atom, and benzoyl optionally substituted by halogen atom or amino) and the like.

The group capable of releasing proton is, for example, preferably carboxyl and tetrazolyl, with particular preference given to carboxyl.

In the formula [II], the alkyl represented by R is preferably linear or branched alkyl having 1 to 6 carbon atoms. Examples of said alkyl include methyl, ethyl, n-propyl, isopropyl, n-butyl, isobutyl, sec-butyl, tert-butyl, n-pentyl, isopentyl, neopentyl and n-hexyl. Preferred is linear or branched alkyl having 1 to 3 carbon atoms. R is particularly preferably isopropyl.

The compound of the formula [I] is preferably a compound of the formula [II], and more preferably a compound of the formula [III].

The compound of the formula [I] can be produced by, for example, reacting a compound of the formula [IV]

[IV]

wherein each symbol is as defined above, and an active methylene compound or acetylenecarboxylic acid derivative, followed by hydrolysis.

Examples of active methylene compound include methyl acetoacetate, ethyl acetoacetate, methyl cyanoacetate, ethyl cyanoacetate, cyanoacetamide, malononitrile, ethyl oxalacetate, diethyl malonate, dimethyl malonate, ethyl benzoylacetate, methyl 3-oxo-n-caproate and the like. These active methylene compounds are used in amounts practically corresponding to about 1 to 10-fold moles per mole of starting compound [IV] or a salt thereof.

Examples of acetylenecarboxylic acid derivative include dimethyl acetylenedicarboxylate, diethyl acetylenedicarboxylate, methyl propiolate, ethyl propiolate and the like. When propiolic acid ester is used, an intermediate aminoacrylate derivative can be isolated. Alternatively, it can be subjected to ring-closing reaction without isolation. These acetylenecarboxylic acid derivatives are used in amounts practically corresponding to about 1 to 10-fold moles per mole of starting compound [IV] or a salt thereof.

In generality, the reaction preferably proceeds in the presence of a base which is exemplified by organic amines such as primary amine (e.g., n-butylamine, benzylamine and aniline), secondary amine (e.g., diethylamine, dipropylamine, dibutylamine, piperidine, pyrrolidine and morpholine), tertiary amine (e.g., 1,8-diazabicyclo[5,4,0]-7-undecene and triethylamine), and heterocyclic base (e.g., imidazole and 2-methylimidazole). These organic bases are used in amounts corresponding to about catalytic amount to 5-fold moles per mole of starting compound [IV] or a salt thereof.

The reaction preferably proceeds in an organic solvent which is exemplified by alcohols such as methanol, ethanol, propanol and butanol, aromatic hydrocarbons such as benzene and toluene, dimethylformamide, and the like. The reaction temperature, reaction time and other conditions for the reaction are not particularly limited. The reaction is generally carried out at a temperature of from room temperature to near boiling point of the solvent used, for about 1 to 24 hours. When desired, amino group of cyanoacetamide, which is an active methylene compound, may be protected in the instant production step. Said protection can be carried out according to a conventional method in the pertinent field.

The conditions of hydrolysis are those for conventional acid hydrolysis. For example, sulfuric acid, hydrochloric acid, phosphoric acid and the like are used in excess and hydrolysis is performed by the action of said acids alone, or in an organic solvent such as organic acids (e.g., formic acid and acetic acid) or alcohols such as methanol, ethanol, propanol and butanol, after which the mixture is generally heated to about 50–150° C. While the reaction time varies depending on the kind of compound to be used, it is generally about 1 hour to several days.

The compound [I] can be also used after being converted to a pharmacologically acceptable salt. Examples of such salt include salts with a base such as inorganic base and organic base and acid addition salts with inorganic acid, organic acid, basic or acidic amino acid and the like.

The inorganic base is exemplified by alkali metals such as sodium and potassium; alkaline earth metals such as calcium and magnesium; aluminum; ammonium and the like.

The organic base is exemplified by primary amine (e.g., ethanolamine), secondary amine (e.g., diethylamine, diethanolamine, dicyclohexylamine and N,N'-dibenzylethylenediamine), tertiary amine (e.g., trimethylamine, triethylamine, pyridine, picoline and triethanolamine), and the like.

The inorganic acid is exemplified by hydrochloric acid, hydrobromic acid, nitric acid, sulfuric acid, phosphoric acid and the like.

The organic acid is exemplified by formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like.

The basic amino acid is exemplified by arginine, lysine and ornithine, and acidic amino acid is exemplified by aspartic acid and glutamic acid.

The salt of compound [I] can be produced according to the method described in, for example, Japanese Patent Unexamined Publication Nos. 10587/1986, 10588/1986 and 88298/1979, U.S. Pat. No. 4,267,332 or a method analogous to these methods.

The compound [I] and a salt thereof have, as is evident from Experimental Examples to be mentioned later, superior therapeutic effect on asthenopia, suppressive action on axial elongation, suppressive action on degradation of retinal functions, and retinal function-recovery action. Therefore, they are useful as agents for the prophylaxis and treatment of disturbance of visual functions.

The agents for the prophylaxis and treatment of disturbance of visual function of the present invention have low toxicity and can be administered safely to mammals such as human, rabbit, dog, cat, cow, horse, monkey and the like by an oral or parenteral route.

The agents for the prophylaxis and treatment of disturbance of visual function of the present invention can be produced by, for example, admixing the compound [I] or a salt thereof with a pharmaceutically acceptable carrier.

The pharmaceutically acceptable carrier includes, for example, various organic and inorganic carriers commonly used as materials for preparations, such as, for solid preparations, excipients, lubricants, binders, disintegrators and the like, and, for liquid preparations, solvents, solubilizers, suspending agents, tackifiers, isotonizing agents, buffers, analgesic agents and the like, which can be used as appropriate. Where necessary, preservatives, chelating agents, antioxidants, colorings, sweeteners, flavors, aromatics, and other additives for preparations may be added by a conventional method.

Examples of suitable excipients include lactose, sucrose, mannitol, starch, crystalline cellulose, light anhydrous silicic acid and the like.

Examples of suitable lubricants include magnesium stearate, calcium stearate, talc, colloidal silica and the like.

Examples of suitable binders include sucrose, mannitol, maltitol, starch, gelatin, gum arabic, tragacanth, crystalline cellulose, dextrin, hydroxypropylcellulose, hydroxypropylmethylcellulose, polyvinylpyrrolidone, sodium arginate, chitin, chitosan and the like.

Examples of suitable disintegrators include starch, carboxymethylcellulose, calcium carboxymethylcellulose, croscarmellose sodium, sodium carboxymethyl starch, chitin, chitosan and the like.

Examples of suitable solvents include water for injection, alcohols (e.g., ethanol, propylene glycol, macrogol, glycerine and the like), fats and oils (e.g., olive oil, sesame oil, peanut oil, cotton seed oil, castor oil, corn oil and the like), and the like.

Examples of suitable solubilizers include polyvinylpyrrolidone, cyclodextrin, caffeine, polyethylene glycol, propylene glycol, mannitol, benzyl benzoate, ethanol, trisaminomethane, cholesterol, triethanolamine, sodium carbonate, sodium citrate and the like.

Examples of suitable suspending agents include surfactants (e.g., stearyl triethanolamine, sodium lauryl sulfate, laurylaminopropionic acid, lecithine, glyceryl monostearate and Polysorbate 80), hydrophilic polymers (e.g., polyvinyl alcohol, polyvinylpyrrolidone, sodium carboxymethylcellulose, methylcellulose, hydroxymethylcellulose, hydroxyethylcellulose, hydroxypropylcellulose, hydroxypropylmethylcellulose, gum arabic, gelatin, albumin, and the like) and the like.

Examples of suitable tackifiers include egg yolk lecithine, gelatin, gum arabic, tragacanth, methylcellulose, sodium carboxymethylcellulose, hydroxyethylcellulose, hydroxypropylcellulose, polyvinyl alcohol, sodium polyacrylate, sodium alginate, pectin and the like.

Examples of suitable isotonizing agents include sorbitol, glycerol, polyethylene glycol, propylene glycol, glucose, sodium chloride and the like.

Examples of suitable buffers include phosphate buffer, borate buffer, citrate buffer, tartrate buffer, acetate buffer and the like.

Examples of suitable analgesic agents include benzyl alcohol and the like.

Examples of suitable preservatives include p-hydroxybenzoate, benzalkonium chloride, benzethonium chloride, chlorobutanol, benzyl alcohol, phenethyl alcohol, dehydroacetic acid, sorbic acid and salt thereof, p-chlorometaxylenol, chlorocresol, thimerosal and the like.

Examples of suitable chelating agents include disodium edetate, sodium citrate, condensed sodium phosphate and the like.

Examples of suitable antioxidants include sulfite, ascorbic acid, c-tocopherol, cysteine and the like.

Examples of suitable colorants include tar pigment, glycyrrhiza extract, riboflavin, zinc oxide and the like.

Examples of suitable sweeteners include glucose, sucrose, fructose, honey, saccharic acid, glycyrrhiza and the like.

Examples of suitable flavors include vanillin, menthol, rose oil and the like.

Examples of suitable aromatics include fennel oil, borneol, menthol and the like.

Besides the above-mentioned, agar, casein, collagen and the like are pharmaceutically acceptable carriers.

Other agents for the prophylaxis and treatment of asthenopia such as a drug containing, as an active ingredient, vitamins (e.g., vitamin $B_1$, vitamin $B_{12}$ and the like), ATP and the like; agents for the prophylaxis and treatment of myopia such as neostigmine methylsulfate, tropicamide and a drug containing these as an active ingredient; other drugs having retinal function-improving action such as tocopherol nicotinate [Juvela N (trademark, manufacture by EISAI CO., LTD.)]; and other ingredients having different efficacy, may be added to the preparation as appropriate.

When the agent for the prophylaxis and treatment of disturbance of visual function of the present invention is used in the form of an aqueous liquid, its pH is 4 to 9 in view of the stability of the compound [I] and a salt thereof.

The oral preparations may be, for example, solid preparations (e.g., powders, granule, tablets and capsules) or liquid preparations (e.g., emulsions, syrups and suspensions).

For example, tablets can be produced by adding the above-mentioned excipients, disintegrators, binders, lubricants and the like as appropriate to compound [I] or a salt thereof and compression formulating the mixture. In so doing, the above-mentioned sweetners, flavors, aromatics and the like may be further added on demand after compression formulation, or coating may be applied by a method known per se for enteric use or controlled release of the preparation. The coating agent used for this end includes, for example, hydroxypropylcellulose, hydroxypropylmethylcellulose, cellulose acetate phthalate, hydroxypropylmethylcellulose phthalate, hydroxypropylmethylcellulose acetate succinate, ethylcellulose and the like.

A suspending agent can be produced by, for example, suspending the compound [I] or a salt thereof in the aforementioned solvent. When desired, the above-mentioned suspending agents may be used as appropriate.

Parenteral preparation includes, for example, injections, preparations for local administration to the eye, and the like. The injection includes subcutaneous injection, intravenous injection, intramuscular injection and the like. Injections may be aqueous or non-aqueous, and a solution or suspension.

The preparations for local administration to the eye include ophthalmic solution, ophthalmic ointment, gel and the like, with particular preference given to ophthalmic solution which may be aqueous or non-aqueous, and a solution or suspension.

The agent for the prophylaxis and treatment of disturbance of visual function of the present invention is preferably used as a preparation for local administration to the eye. More preferably, it is used as an ophthalmic solution, particularly an aqueous ophthalmic solution.

An aqueous injection can be prepared by, for example, dissolving compound [I] or a salt thereof in water for injection together with the above-mentioned preservatives, isotonizing agents, solubilizers and the like. An oily injection can be prepared by dissolving or suspending compound [I] or a salt thereof in propylene glycol, olive oil, sesame oil, cotton seed oil and the like.

An aqueous ophthalmic solution can be prepared by, for example, heating distilled water, dissolving a preservative therein, adding a solubilizer, and adding and completely dissolving compound [I] or a salt thereof. Where necessary, buffers, isotonizing agents, chelating agents, tackifiers and the like may be also added.

The solubilizer is preferably polyvinylpyrrolidone, cyclodextrin, caffeine and the like, with particular preference given to polyvinylpyrrolidone. When polyvinylpyrrolidone is used, compound [I] and a salt thereof are noticeably improved in solubility and come to have greater stability [see Japanese Patent Unexamined Publication No. 123116/1987, i.e., Japanese Patent Examined Publication No. 78614/1992].

For example, polyvinylpyrrolidone to be used has an average molecular weight of about 25,000 to about 120,000, preferably about 40,000 (e.g., polyvinylpyrrolidone K30). Polyvinylpyrrolidone is generally added in a concentration of 0.2 to 20 (W/V) %, preferably 0.5 to 15 (W/V) %, particularly preferably 1 to 10 (W/V) %.

The buffer is particularly preferably a borate buffer. When borate buffer is used, a less irritant liquid as compared to other buffers, such as phosphate buffer, can be obtained. In this case, boric acid is added in a concentration of 0.2 to 4 (W/V) %, preferably 0.5 to 2 (W/V) %.

The aqueous ophthalmic suspension can be prepared by adding, besides the above-mentioned additives used for aqueous ophthalmic solutions, the aforementioned suspending agents as appropriate.

The pH of the above-mentioned aqueous ophthalmic solution and aqueous ophthalmic suspension is preferably 4 to 9, particularly preferably 5 to 8.

A non-aqueous ophthalmic solution can be prepared by dissolving or suspending compound [I] or a salt thereof in an aqueous solvent such as alcohols (e.g., ethanol, ethylene glycol, macrogol, propylene glycol, glycerol and the like) and an oily solvent such as fats and oils (e.g., olive oil, sesame oil, peanut oil, cotton seed oil, castor oil, corn oil and the like).

An ophthalmic ointment can be prepared by appropriately using, for example, petrolatum, plastibase, liquid paraffin and the like as a base.

An ophthalmic gel can be prepared by appropriately using, for example, carboxyvinyl polymer, polymer of ethylene maleic anhydride, polyoxyethylene-polyoxypropylene block copolymer, gellan gum and the like as a base.

While the dose of the agent for the prophylaxis and treatment of disturbance of visual function of the present invention varies depending on the administration route, kind of diseases, symptoms, age and body weight of patients, and the like, for example, it is preferably administered to an adult patient with asthenopia, axial myopia or retinal disease as an aqueous ophthalmic solution comprising compound [I] or a salt thereof, which is an active ingredient, in a concentration of 0.01 to 2.0 (W/V) %, preferably 0.1 to 1.0 (W/V) %, in a single dose of one to several drops thereof according to symptoms, once to several times a day, preferably 2 to 5 times a day, to one eye of a patient.

The present invention is described in more detail in the following by way of Examples, and the effects of the invention are clarified by way of Experimental Examples, which should not be construed as limiting the invention.

EXAMPLE 1

Aqueous Ophthalmic Solution (Formulation)

| | |
|---|---|
| compound [III] | 5 g |
| boric acid | 9 g |
| sodium tetraborate | 16 g |
| polyvinylpyrrolidone K30 | 20 g |
| methyl p-hydroxybenzoate | 0.26 g |
| propyl p-hydroxybenzoate | 0.14 g |
| hydrochloric acid | suitable amount |
| sterile purified water | amount to make the total 1,000 ml (pH 6.0) |

(Preparation Method)

Sterile purified water (800 ml) was heated and methyl p-hydroxybenzoate and propyl p-hydroxybenzoate were dissolved therein. Then, boric acid, sodium tetraborate, polyvinylpyrrolidone K30 and compound [III] were successively added and dissolved. After cooling, hydrochloric acid was added to adjust the pH to 6.0 and sterile purified water was added to make the total amount 1,000 ml. The mixture was sterilized by filtration through a 0.22 μm membrane filter and filled in a predetermined container to give an aqueous ophthalmic solution.

EXAMPLE 2

Aqueous Ophthalmic Solution (Formulation)

| | |
|---|---|
| compound [III] | 5 g |
| boric acid | 16 g |
| sodium tetraborate | 10 g |
| polyvinylpyrrolidone K30 | 20 g |
| caffeine | 2 g |
| polyethylene glycol (average molecular weight 4,000) | 5 g |
| methyl p-hydroxybenzoate | 0.26 g |
| propyl p-hydroxybenzoate | 0.14 g |
| hydrochloric acid | suitable amount |
| sterile purified water | amount to make the total 1,000 ml (pH 6.0) |

(Preparation Method)

Sterile purified water (800 ml) was heated and methyl p-hydroxybenzoate and propyl p-hydroxybenzoate were dissolved therein. Then, boric acid, sodium tetraborate, polyvinylpyrrolidone K30, caffeine, polyethylene glycol and compound [III] were successively added and dissolved. After cooling, hydrochloric acid was added to adjust the pH to 6.0 and sterile purified water was added to make the total amount 1,000 ml. The mixture was sterilized by filtration through a 0.22 μm membrane filter and filled in a predetermined container to give an aqueous ophthalmic solution.

EXAMPLE 3

Aqueous Ophthalmic Solution (Formulation)

| | |
|---|---|
| compound [III] | 2.5 g |
| boric acid | 16 g |
| sodium tetraborate | 7 g |
| polyvinylpyrrolidone K30 | 20 g |
| methyl p-hydroxybenzoate | 0.26 g |
| propyl p-hydroxybenzoate | 0.14 g |
| sodium hydroxide | suitable amount |
| sterile purified water | amount to make the total 1,000 ml (pH 7.5) |

(Preparation Method)

Sterile purified water (800 ml) was heated, and methyl p-hydroxybenzoate and propyl p-hydroxybenzoate were dissolved therein by heating and the solution was cooled to room temperature. Then, boric acid, sodium tetraborate and polyvinylpyrrolidone K30 were successively added and dissolved. Compound [III] was added and dissolved therein. Sodium hydroxide was added to adjust the pH to 7.5 and sterile purified water was added to make the total amount 1,000 ml. The mixture was sterilized by filtration through a 0.22 μm membrane filter and filled in a predetermined container to give an aqueous ophthalmic solution.

EXAMPLE 4

Aqueous Ophthalmic Solution (Formulation)

| | |
|---|---|
| compound [III] | 5 g |
| boric acid | 16 g |
| sodium tetraborate | 7 g |
| polyvinylpyrrolidone K30 | 20 g |
| methyl p-hydroxybenzoate | 0.26 g |
| propyl p-hydroxybenzoate | 0.14 g |
| sodium hydroxide | suitable amount |
| sterile purified water | amount to make the total 1,000 ml (pH 8.0) |

(Preparation Method)

Sterile purified water (800 ml) was heated, and methyl p-hydroxybenzoate and propyl p-hydroxybenzoate were dissolved therein by heating and the solution was cooled to room temperature. Then, boric acid, sodium tetraborate and polyvinylpyrrolidone K30 were successively added and dissolved. Compound [III] was added and dissolved therein. Sodium hydroxide was added to adjust the pH to 8.0 and sterile purified water was added to make the total amount 1,000 ml. The mixture was sterilized by filtration through a 0.22 μm membrane filter and filled in a predetermined container to give an aqueous ophthalmic solution.

EXAMPLE 5

Aqueous Ophthalmic Solution (Formulation)

| | |
|---|---|
| compound [III] | 10 g |
| boric acid | 16 g |
| sodium tetraborate | 7 g |
| polyvinylpyrrolidone K30 | 20 g |
| methyl p-hydroxybenzoate | 0.26 g |
| propyl p-hydroxybenzoate | 0.14 g |
| sodium hydroxide | suitable amount |
| sterile purified water | amount to make the total 1,000 ml (pH 8.0) |

(Preparation Method)

Sterile purified water (800 ml) was heated, and methyl p-hydroxybenzoate and propyl p-hydroxybenzoate were dissolved therein by heating and the solution was cooled to room temperature. Then, boric acid, sodium tetraborate and polyvinylpyrrolidone K30 were successively added and dissolved. Compound [III] was added and dissolved therein.

Sodium hydroxide was added to adjust the pH to 8.0 and sterile purified water was added to make the total amount 1,000 ml. The mixture was sterilized by filtration through a 0.22 μm membrane filter and filled in a predetermined container to give an aqueous ophthalmic solution.

EXAMPLE 6

Aqueous Ophthalmic Suspension (Formulation)

| | |
|---|---|
| compound [III] | 10 g |
| sodium dihydrogenphosphate | 50 g |
| sodium chloride | 9 g |
| polysorbate 80 | 20 g |
| chlorobutanol | 3 g |
| sodium hydroxide | suitable amount |
| sterile purified water | amount to make the total 1,000 ml (pH 5.0) |

(Preparation Method)

Sterile purified water (800 ml) was heated, and chlorobutanol was dissolved therein. Then, sodium dihydrogenphosphate, sodium chloride and polysorbate 80 were successively added and dissolved. The solution was cooled to room temperature. Sodium hydroxide was added to adjust the pH to 5.0 and sterile purified water was added to make the total amount 1,000 ml. The mixture was sterilized by filtration through a 0.22 μm membrane filter, thereby to uniformly disperse compound [III] sterilized in advance, whereby an aqueous ophthalmic suspension was prepared.

EXAMPLE 7

Oily Ophthalmic Solution (Formulation)

| | |
|---|---|
| compound [III] | 20 g |
| cotton seed oil | amount to make the total 1,000 ml |

(Preparation Method)

Compound [III] was added to cotton seed oil sterilized in advance to give an oily ophthalmic solution.

EXAMPLE 8

Ophthalmic Ointment (Formulation)

| | |
|---|---|
| compound [III] | 10 g |
| liquid paraffin | 100 g |
| white petrolatum | amount to make the total 1,000 g |

(Preparation Method)

Liquid paraffin and white petrolatum were sterilized by heating in advance. Then, compound [III] was thoroughly admixed with liquid paraffin and then sufficiently admixed with white petrolatum to give an ophthalmic ointment.

EXAMPLE 9

Ophthalmic Gel (Formulation)

| | |
|---|---|
| compound [III] | 5 g |
| carboxyvinyl polymer | 10 g |
| phenethyl alcohol | 5 g |
| sodium hydroxide | suitable amount |
| sterile purified water | amount to make the total 1,000 g (pH 7.0) |

(Preparation Method)

Phenethyl alcohol was dissolved in sterile purified water (800 ml) and sterilized by filtration through a 0.22 μm membrane filter. Compound [III] sterilized in advance was suspended in this solution and the suspension was vigorously stirred, during which sterilized carboxyvinyl polymer was added and dissolved. The obtained solution was adjusted to pH 7.0 with sodium hydroxide, and sterile purified water was added to make the total amount 1,000 g to give an ophthalmic gel.

EXAMPLE 10

Tablet (Formulation)

| | |
|---|---|
| compound [III] | 10 mg |
| lactose | 35 mg |
| corn starch | 150 mg |
| microcrystalline cellulose | 30 mg |
| magnesium stearate | 5 mg |
| per tablet | 230 mg |

(Preparation Method)

Compound [III], lactose, corn starch, ⅔ amount of microcrystalline cellulose and ½ amount of magnesium stearate were admixed and granulated. The rest of microcrystalline cellulose and magnesium stearate was added and the mixture was compression formed to give tablets.

EXAMPLE 11

Capsule (Formulation)

| | |
|---|---|
| compound [III] | 10 mg |
| lactose | 90 mg |
| microcrystalline cellulose | 70 mg |
| magnesium stearate | 10 mg |
| per capsule | 180 mg |

(Preparation Method)

Compound [III], lactose, microcrystalline cellulose and ½ amount of magnesium stearate were admixed and granulated. The rest of magnesium stearate was added and the mixture was concealed in gelatin capsules to give capsules.

EXAMPLE 12

Injection (Formulation)

|  |  |
| --- | --- |
| compound [III] | 10 mg |
| inositol | 100 mg |
| benzyl alcohol | 20 mg |
| per ampoule | 130 mg |

(Preparation Method)

Compound [III], inositol and benzyl alcohol were dissolved in distilled water for injection to the total amount of 2 ml and the solution was concealed in an ampoule. The entire procedure was carried out under sterile conditions.

EXPERIMENTAL EXAMPLE 1

Therapeutic Effect on Asthenopia by Administration of the Agent of the Invention to Patients with Asthenopia According to the near point determination method proposed by Taturo Himi [Drug Effect on Asthenopia-Analysis of Drug Effect by Age, *Atarashii Ganka* (Journal of the Eye), vol. 3, No. 9, pp. 1247–1253 (1986)], therapeutic effect of the preparation of the present invention on asthenopia was investigated.

Six patients A–F (age 20–26) who visited hospital for asthenopia underwent instillation of the preparation of the present invention (aqueous ophthalmic solution obtained in Example 1) into one eye and placebo (aqueous ophthalmic solution prepared by removing the main drug, compound [III], from the preparation of the present invention) into the other eye by 2 drops per time and four times a day (9 o'clock, 13 o'clock, 17 o'clock and 21 o'clock), which was continued for 14 days. The patients A to F underwent 10 repeats of near point determination using an accommodopolyrecorder HS-9E equipped with continuous near pointometer (manufactured by Kowa Corp.) before instillation, and 7 and 14 days after instillation. Note that the values used for the evaluation this time were near point disappearance values, and the distance to the point(position) at which a near point table (index) drawing near blurred was recorded as the determination values. This is somewhat different from the measurement method generally employed. The reason this method was employed was that, from experience, this method is known to give stable and most fine responses when test subjects have different age, educational and environmental backgrounds (see publication supra, pp. 1248 and 1252).

Then, mean (M) and standard error (SD) of the near point as determined 10 times in the above with respect to the preparation of the present invention and placebo were calculated, and based on the obtained results, coefficient of variation CV (SD/M) was calculated. It is known that the progression of asthenopia leads to greater CV values. The average coefficients of variation (CV) of the six patients A–F was calculated with respect to the results obtained before instillation (day 0), 7 days after instillation and 14 days after instillation, and CV (T)/CV (0) (where T is 7 or 14) of the preparation of the present invention and placebo was calculated using the average of coefficient of variation before instillation (day 0) as CV (0), and that of 7 days after instillation and 14 days after instillation as CV (T) where T is 7 or 14. The results are shown in Table 1 and FIG. 1.

TABLE 1

| | CV (T)/CV (0) at 7 days and 14 days after instillation of test drug | |
| --- | --- | --- |
| test drug | 7 days after instillation CV (7)/CV (0) | 14 days after instillation CV (14)/CV (0) |
| preparation of invention | 0.78 | 0.87 |
| placebo | 1.02 | 1.12 |

Figure 1:
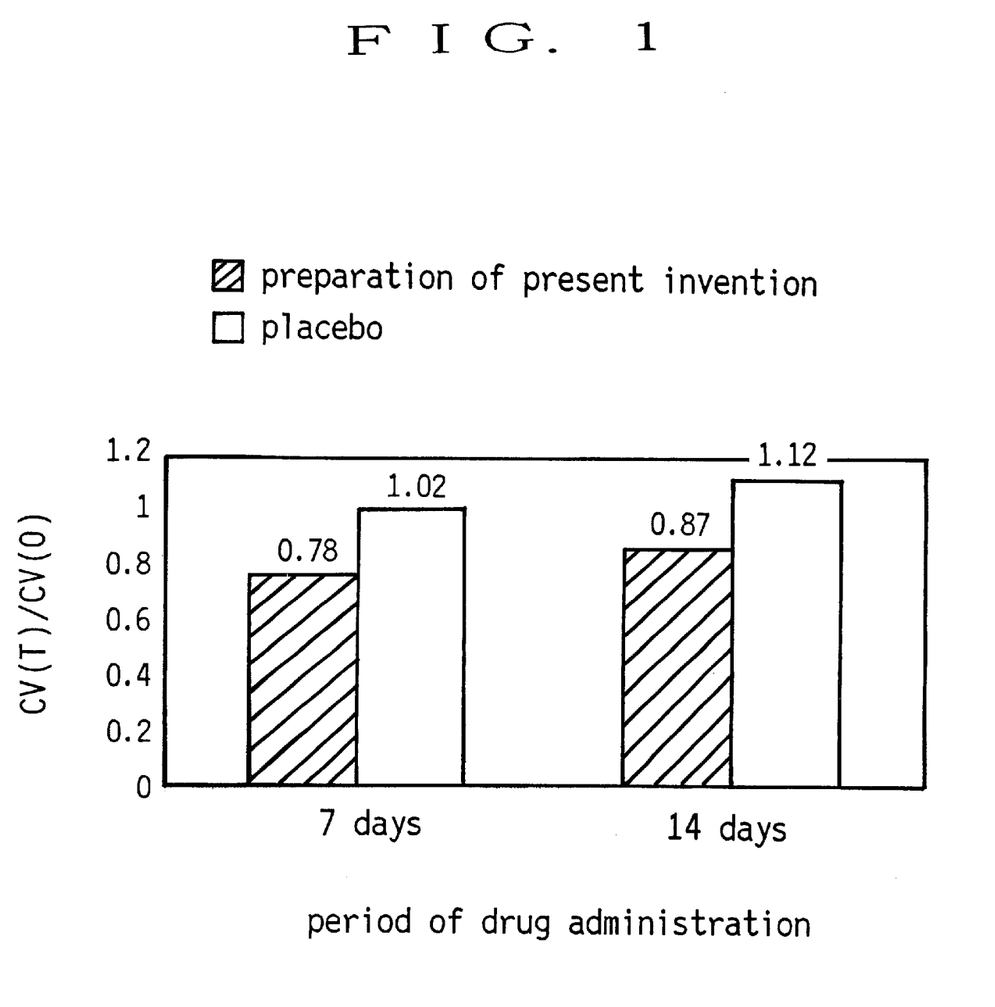
FIG. 1 is a graph showing CV(T)/CV(0) as determined in Experimental Example 1 with regard to coefficient of variation (CV) of 6 patients A to F before administration of test drug (Day 0), 7 days and 14 days after administration thereof, wherein the average coefficient of variation before administration (Day 0) is CV(0) and the average coefficient of variation at 7 days and 14 days after administration is CV(T) wherein T is 7 or 14. In the Figure, the horizontal axis shows the period of drug administration (7 days and 14 days) and the vertical axis shows CV(T)/CV(0).

As is evident from Table 1 and FIG. 1, the eyes instilled with the preparation of the present invention showed lower CV values (smaller than 1) at 7 days and 14 days after instillation, as compared to that before instillation. In contrast, the eyes instilled with placebo did not show decrease in CV values (greater than 1). Thus, the preparation of the present invention showed superior therapeutic effect on asthenopia in clinical tests, and was found to be clinically useful for the treatment of asthenopia.

EXPERIMENTAL EXAMPLE 2

Therapeutic Effect on Axial Myopia by Administration of the Agent of the Invention (Method)

As test animals, 7 days old male white leghorn chicks were used. The chicks were raised under 12 hour (8:00–20:00) lighting of 600 lux illumination. A mixture of ketamine hydrochloride [Ketalar (trademark, Sankyo Company, Limited)] and xylazine hydrochloride [Celactal (trademark, Bayer, Ltd.)] was intramuscularly injected to the chicks for general anesthesia. The upper and lower eyelids of one eye were sutured at the edge (hereinafter the eye sutured in this way may be referred to as sutured eye). At 4 days post-suture, the eyelids were opened and anterior chamber depth, lens thickness and vitreous chamber depth of both eyes were measured using A scan mode ultrasound (Z-1000, General). As a test drug, an aqueous ophthalmic solution containing compound [III] (content 0.5% and 1%) obtained in Examples 4 and 5 was subconjunctivally administered by 10 $\mu$l under ether anesthesia to the sutured eye twice on the day of suture and measurement day, and 4 times a day from day 1 to day 3. In the same manner, physiological saline was subconjunctivally administered to the sutured eye of the control group. The other eye of the chicks of both groups was untreated to suture and administration of the test drug (hereinafter the other eye may be referred to as non-sutured eye).

(Results)

The difference in vitreous chamber depth of sutured eye and non-sutured eye at 4 days post-suture is shown in Table 2.

TABLE 2

| | vitreous chamber depth (mm) | |
| --- | --- | --- |
| group | sutured eye - non-sutured eye | n |
| physiological saline | 0.46 ± 0.03 | 25 |
| aqueous ophthalmic solution of Ex. 4 (0.5% compound [III]) | 0.37 ± 0.03* | 25 |
| aqueous ophthalmic solution of Ex. 5 (1% compound [III]) | 0.34 ± 0.03* | 25 |

*significance level less than 5% by Student's t-test

The vitreous chamber depth of control group at 4 days after eyelid suture was 0.46 mm significantly longer than that of non-sutured eye. The difference between sutured eye and non-sutured eye of the group administered with 0.5% and 1% compound [III] was 0.37 and 0.34 mm, respectively. Thus, compound [III] significantly suppressed elongation of vitreous chamber depth. As regards anterior chamber depth and lens thickness, no difference was observed between sutured eye and non-sutured eye of the control group and the group administered with compound [III].

From the above results, it is evident that compound [III] suppressed elongation of vitreous chamber depth due to eyelid suture in chick eyes.

The pharmaceutical preparation of the present invention significantly suppressed elongation of vitreous chamber depth due to eyelid suture in chick eyes. The involvement of retinal neurotransmitter is speculated in the onset mechanism of myopia induced by eyelid suture, though not yet fully elucidated. Most of the changes seen in model with axial myopia, such as elongation of vitreous chamber depth, extension of sclera, and thinning of choroid and retinal pigment epithelial layer, resembles the changes found in myopia of human. Inasmuch as compound [III] suppressed elongation of vitreous chamber depth in the instant models, the pharmaceutical preparation of the present invention is considered to be effective for the prevention and treatment of axial myopia in human.

EXPERIMENTAL EXAMPLE 3

Suppression of Decrease of Retinal Function by Administration of the Agent of the Invention (Method)

ERG (electroretinogram) which is one of the methods to examine retinal functions can detect action potential of retina in response to light, from the surface of an eyeball. When a retinal disorder occurs, extension of peak latency and reduced amplitude are found. Inasmuch as ERG changes in central retinal artery and vein occlusions, congenital stationary night blindness, diabetic retinopathy, pigmentary retinal degeneration, retinal detachment, uveitis and the like, it has been used as useful objective auxiliary diagnostic of these diseases. Meanwhile, a report has documented that eye-occluded chicks showed the reduction of amplitude of oscillatory potential in ERG and thinning of retina (Takashi Fujikado, *Nihon Ganka Kiyo*, 42:1189–1194, 1991).

In this Experimental Example, white leghorn chicks were used as test animals, and action potential of retina was induced and recorded by ERG to evaluate retinal functions. The method therefor are described in the following.

The chicks were raised under 12 hour (8:00–20:00) lighting of 600 lux illumination at temperature 31±3° C. humidity 50±10%. Six days old chicks were accommodated in a complete dark room for 30 minutes, and a 1:1 mixture of ketamine hydrochloride [Ketalar (trademark, Sankyo Company, Limited)] and xylazine hydrochloride [Celactal (trademark, Bayer, Ltd.)] was intramuscularly injected to the chicks by 10 μl per 10 g body weight for general anesthesia. The head was fixed in a brain stereotaxis apparatus, and different and indifferent electrodes were respectively connected to the center of cornea and bulbar conjunctiva of the left eye by the use of a 0.5 mm diameter platinum wire, with grounding electrode led from under the skin of the head. After acclimation in the dark for one minute, 3 joule xenon light was irradiated 8 times from 20 cm before the cornea at 10-second intervals, and the averaged consecutive responses were evaluated using a potential recorder. The ERG obtained here is taken as the initial value.

A mixed solution of ketamine hydrochloride and xylazine hydrochloride was intramuscularly injected to the chicks for general anesthesia. The upper and lower eyelids were cut off under a stereoscopic microscope, and the left eye was sutured 5 stitches using 8-0 silk suture thread with needle (hereinafter the eye sutured in this way may be referred to as sutured eye).

As the test drug, compound [III] was dissolved in 0.1 M $NaH_2PO_4$ (pH 10) solution to a concentration of 0.5% (pH 7.8 after adjustment) and intraperitoneally administered 3 times a day on the day and the next day of suture, and once a day at two days after suture. The dose was 50 mg/kg. In the same manner, physiological saline was administered to the control group.

At 2 days post-suture, ERG was taken in the same manner as above after administration of the drug, and the averaged consecutive responses were evaluated using a potential recorder.

Figure 2:
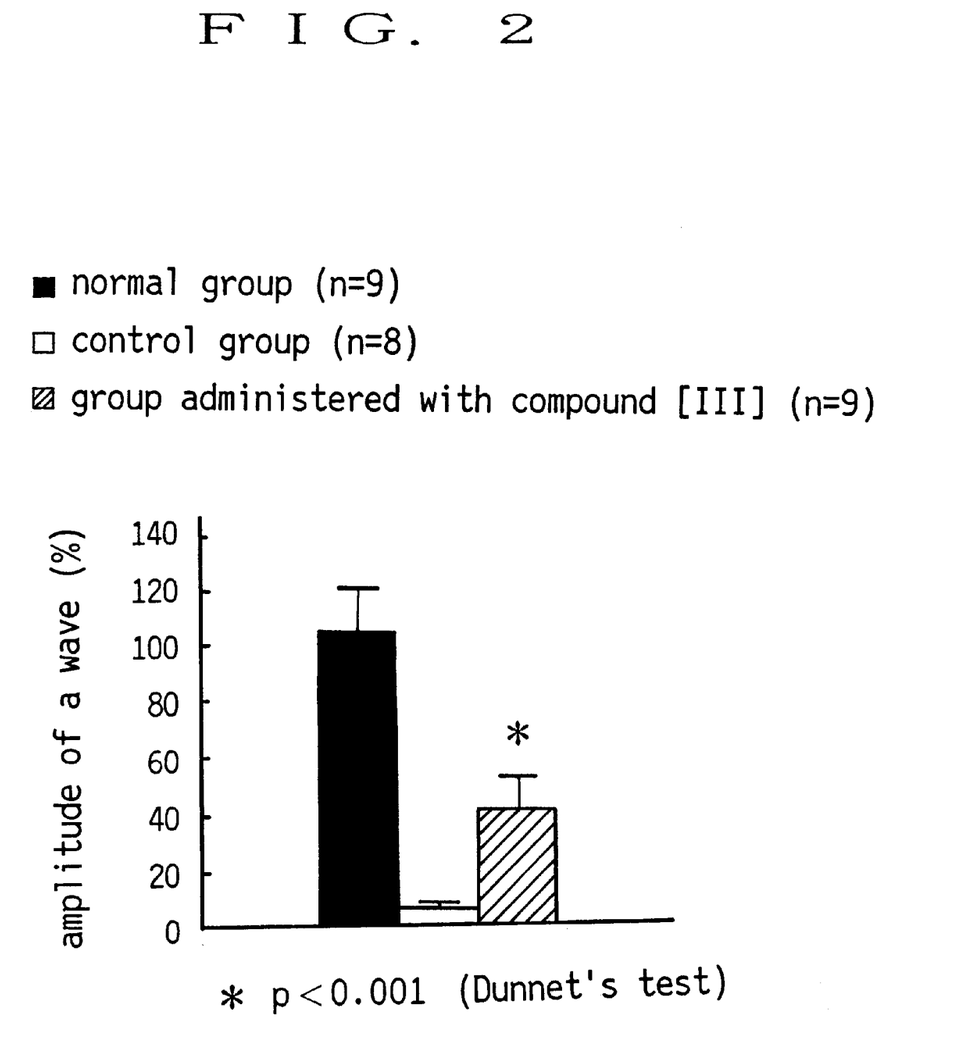
FIG. 2 shows amplitude of a wave of ERG at 2 days after eyelid suture, wherein each column shows mean±standard error.
Figure 3:
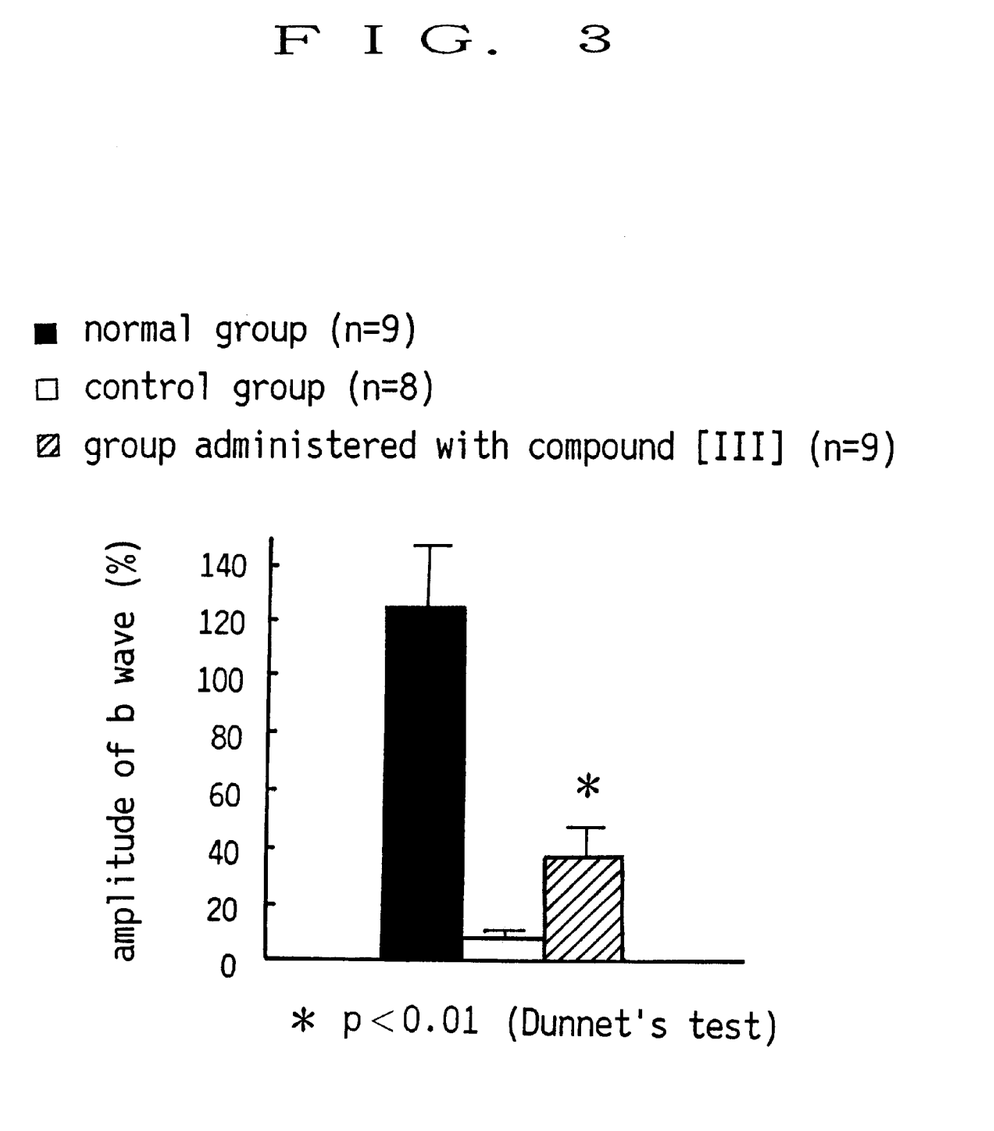
FIG. 3 shows amplitude of b wave of ERG at 2 days after eyelid suture, wherein each column shows mean±standard error.
Figure 4:
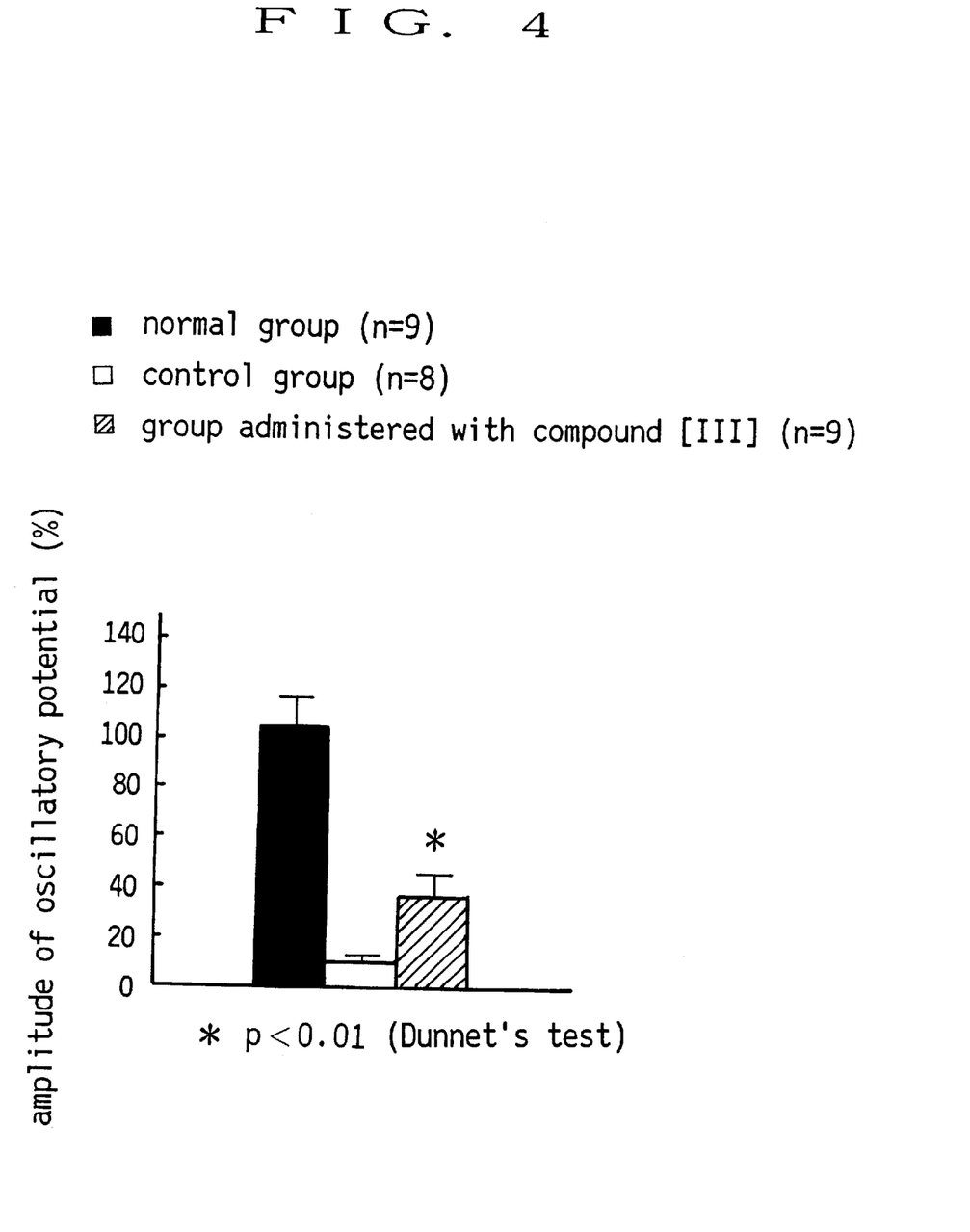
FIG. 4 shows amplitude of oscillatory potential of ERG at 2 days after eyelid suture, wherein each column shows mean±standard error.

The a wave amplitude of ERG as determined at 2 days post-suture is shown in FIG. 2; b wave amplitude is shown in FIG. 3; and amplitude of oscillatory potential is shown in FIG. 4. The amplitude of a wave decreased to 6% of the initial value as a result of eyelid suture. In contrast, the group administered with compound [III] showed decrease to 42% of the initial value, thus showing significant suppression of amplitude decrease as compared to the control group. The amplitude of b wave decreased to 8% of the initial value as a result of eyelid suture. In contrast, the group administered with compound [III] showed decrease to 37% of the initial value, thus showing significant suppression of amplitude decrease as compared to the control group. The amplitude of oscillatory potential decreased to 10% of the initial value as a result of eyelid suture. In contrast, the group administered with compound [III] showed decrease to 37% of the initial value, thus showing significant suppression of amplitude decrease as compared to the control group.

From these results, it is appreciated that compound [III] significantly suppressed decrease of the amplitude of a wave, b wave and oscillatory potential of ERG caused by eyelid suture of chick eyes. Therefrom it is clear that compound [III] suppresses lowering of retinal functions, and therefore, the pharmaceutical agent of the present invention is useful as an agent for the prophylaxis and treatment of retinal diseases.

The agent for the prophylaxis and treatment of disturbance of visual function of the present invention has superior preventive and therapeutic effect on asthenopia, and shows suppression of axial elongation, suppression of degradation of retinal functions and retinal function-recovery action. Hence, the agent can be advantageously used as a clinically applicable agent for the prophylaxis and treatment of disturbance of visual function.

This application is based on application Nos. 176933/1996, 213941/1996 and 314033/1996 filed in Japan, the contents of which are incorporated hereinto by reference.

What is claimed is:

1. A method for the treatment of disturbance of visual function selected from the group consisting of asthenopia and retinal diseases, which comprises administering a pharmaceutically effective amount of a compound of the formula (I)

(I)

wherein
A ring is optionally substituted;
R₁ is a hydrogen or an optionally protected amino; and
R₂ is a group capable of releasing a proton,
or salt thereof to a patient in need thereof.

2. The method according to claim 1, wherein the A ring is optionally substituted by halogen atom, nitro, alkyl, alkoxy or butadienylene (—CH═CH—CH═CH—) which forms a benzene ring with two adjacent carbon atoms at two of the 6, 7, 8 and 9 positions.

3. The method according to claim 1, wherein the group capable of releasing a proton is carboxyl or tetrazolyl.

4. The method according to claim 1, wherein the compound is represented by the formula [II]

[II]

wherein
R is an alkyl;
R₁ is a hydrogen or an optionally protected amino; and
R₂ is a group capable of releasing a proton.

5. The method according to claim 4, wherein the alkyl has 1 to 6 carbon atoms.

6. The method according to claim 4, wherein the alkyl is isopropyl.

7. The method according to claim 1 or claim 4, wherein R₁ is an amino.

8. The method according to claim 1 or claim 4, wherein R₂ is a carboxyl.

9. The method according to claim 1, wherein the compound is represented by the formula [III]

[III]

10. The method according to claim 1, comprising local administration of the compound of the formula [I] or a salt thereof to the eye.

11. The method according to claim 1, comprising administering the compound of the formula [I] or a salt thereof in the form of a liquid preparation.

12. The method according to claim 10, comprising administering the compound of the formula [I] or a salt thereof in the form of an ophthalmic solution.

13. The method according to claim 12, wherein the ophthalmic solution is an aqueous ophthalmic solution.

14. The method according to claim 11, comprising administering the compound of the formula [I] or a salt thereof in the form of an injection.

15. The method according to claim 13 or claim 14, comprising administering the compound of the formula [I] or a salt thereof in the presence of a solubilizer.

16. The method according to claim 15, wherein the solubilizer is polyvinylpyrrolidone.

17. The method according to claim 16, wherein the polyvinylpyrrolidone is contained in a concentration of 0.2–20 (W/V) %.

18. The method according to claim 13 or claim 14, comprising administering a pharmaceutical preparation containing the compound of the formula [I] or a salt thereof in a concentration of 0.01–2.0 (W/V) %.

* * * * *

UNITED STATES PATENT AND TRADEMARK OFFICE
CERTIFICATE OF CORRECTION

PATENT NO. : 5,952,338
DATED : September 14, 1999
INVENTOR(S) : Tsuboi et al

It is certified that error appears in the above-identified patent and that said Letters Patent is hereby corrected as shown below:

ON THE TITLE PAGE, UNDER FOREIGN PAGENT DOCUMENTS:

For 61010587, the date which reads "3/1981" should read --1/1986--.

For 61010588, the date which reads "3/1981" should read --1/1986--.

Signed and Sealed this

Twenty-ninth Day of August, 2000

Attest:

Q. TODD DICKINSON

*Attesting Officer*   *Director of Patents and Trademarks*